United States Patent [19]
Michelsen et al.

[11] Patent Number: 6,143,543
[45] Date of Patent: Nov. 7, 2000

[54] ENZYME SYSTEM COMPRISING FERULIC ACID ESTERASE FROM ASPERGILLUS

[75] Inventors: Birgit Michelsen, Frederiksberg, Denmark; Ronald Peter De Vries; Jacob Visser, both of Wageningen, Netherlands; Jørn Borch Søe, Mundelstrup, Denmark; Charlotte Horsmans Poulsen, Braband, Denmark; Masoud R. Zargahi, Aarhus, Denmark

[73] Assignee: Danisco A/S, Copenhagen, Denmark

[21] Appl. No.: 08/975,600

[22] Filed: Nov. 21, 1997

[51] Int. Cl.$^7$ .................................. C12N 9/16; C12N 9/98
[52] U.S. Cl. ........................ 435/196; 435/187; 435/189; 435/195; 435/197
[58] Field of Search .................................. 435/195, 196, 435/197, 252–33, 255–3, 320.1, 187, 189; 536/23.1, 23.2, 23.7

[56] References Cited

U.S. PATENT DOCUMENTS 5,707,847   1/1998   Christgau et al. ................... 435/197

OTHER PUBLICATIONS de Vries et al. "The faeA genes from *Aspergillus niger* and *Aspergillus tubingensis* encode ferulic acid esterase involved in degradation of complex cell wall polysaccharides" App. Environ. Microbiol. 63 (12), 4638–4644, Dec. 1997.

Faulds et al. "Purification and characterization of a ferulic acid esterase (FAE–III) from *Aspergillus niger*: specificity for the phenolic moity to microcrystalline cellulose" Microbiology 140, 799–787, 1994.

Faulds et al. "Ferulic acid esterase from *Aspergillus niger*: purification and partial characterization of two forms from commercial source of pectinase" Biotechnol. App. Biochem. 17, 349–359, Jun. 1993.

Graf, E. "Antoxidant potential of ferulic acid" Free Radical Biol. Med. 13, 435–448, 1992.

Ralet et al. "Degradation of feryloylated oligosaccharides from sugar–beet pulp and wheat bran by ferulic acid esterase from *Aspergillus niger*" Carbohyd. Res. 263, 257–269, 1994.

Faulds et al. "Release of ferulic acid from plant polysaccharides by ferulic acid esterase from *Streptomyces olivochromogenes*," Carbohydrate Polymers 21:153–55 (1993).

Faulds et al. "Ferulic acid release from plant polysaccharides by specific esterases," in Xylans and Xylanases (ed by J. Visser et al., Elseveier Science Publishers 1992).

*Primary Examiner*—Nashaat T. Nashed
*Attorney, Agent, or Firm*—Frommer Lawrence & Haug, LLP; Thomas J. Kowalski

[57] ABSTRACT

An enzyme system is described that is useful for preparing food and feed. One enzyme of that system is obtainable from Aspergillus. That enzyme has the following characteristics: a MW of from 29 kDa to 36 kDa as measured on a SDS-Phastgel (10–15%) or about 30 kDa; a pI value of about 3–4; ferulic acid esterase activity; a pH optimum of about 5; and a temperature optimum of from about 50 to about 60° C.

8 Claims, No Drawings

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 59 amino acids
      (B) TYPE: amino acid
      (C) STRANDEDNESS: Not Relevant
      (D) TOPOLOGY: linear (ii) MOLECULE TYPE: amino acid (xi) SEQUENCE DESCRIPTION: SEQ ID NO:1:

Ala Ser Thr Gln Gly Ile Ser Glu Asp Leu Tyr Thr Arg Leu Val Glu
1               5                   10                  15

Met Ala Thr Ile Ser Gln Ala Ala Tyr Ala Asp Leu Xaa Asn Ile Pro
                20                  25                  30

Ser Thr Ile Ile Lys Gly Glu Lys Ile Tyr Asn Ser Gln Thr Asp Ile
            35                  40                  45

Asn Gly Trp Ile Leu Arg Asp Asp Ser Ser Lys
        50                  55

(2) INFORMATION FOR SEQ ID NO:2:

(i) SEQUENCE CHARACTERISTICS:
      (A) LENGTH: 46 amino acids
      (B) TYPE: amino acid
      (C) STRANDEDNESS: Not Relevant (D) TOPOLOGY: linear (ii) MOLECULE TYPE: amino acid (xi) SEQUENCE DESCRIPTION: SEQ ID NO:2:

Ser Leu Val Lys Gln Gln Val Ser Gln Tyr Pro Asp Tyr Ala Leu Thr
1               5                   10                  15

Val Thr Gly His Ser Leu Gly Ala Ser Leu Ala Ala Leu Thr Ala Ala
                20                  25                  30

Gln Leu Ser Ala Thr Tyr Asp Asn Ile Arg Leu Tyr Thr Phe
        35                  40                  45

(2) INFORMATION FOR SEQ ID NO:3:

(i) SEQUENCE CHARACTERISTICS:
        (A) LENGTH: 27 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:3:

Glu Ile Ile Thr Val Phe Arg Gly Thr Gly Ser Asp Thr Asn Leu Gln
1               5                   10                  15

Leu Asp Thr Xaa Tyr Thr Leu Xaa Pro Phe Asp
            20                  25

(2) INFORMATION FOR SEQ ID NO:4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (D) OTHER INFORMATION: Note: nucleotide at pos. 7 is inosine (xi) SEQUENCE DESCRIPTION: SEQ ID NO:4:

CARACGNAYA THAAYGGNTG GAT                                        23

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GCRTARTCNG GRTAYTG                                               17

(2) INFORMATION FOR SEQ ID NO:6:

(i) SEQUENCE CHARACTERISTICS:
        (A) LENGTH: 244 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:6:

```
CAGACGGAAT AAACGGATGG ATCCTCCGCG ACGACACCAG CAAAGAAATT ATCACCGTCT      60

TCCGTGGCAC TGGCAGTGAC ACAAACCTAC AGCTCGATAC TAACTACACG CTCACGCCAT     120

TCGACACTCT ACCTCAATGC AACGATTGCG AGGTACACGG TGGATACTAT ATTGGATGGA     180

TCTCAGTCCA AGACCAAGTC GAGTCGCTTG TCAAACAACA GGCTAGCCAG TATCCTGACT     240

ATGC                                                                 244
```

(2) INFORMATION FOR SEQ ID NO:7:

(i) SEQUENCE CHARACTERISTICS:
        (A) LENGTH: 77 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:7:

```
Ile Asn Gly Trp Ile Leu Arg Asp Asp Thr Ser Lys Glu Ile Ile Thr
1               5                   10                  15

Val Phe Arg Gly Thr Gly Ser Asp Thr Asn Leu Gln Leu Asp Thr Asn
            20                  25                  30

Tyr Thr Leu Thr Pro Phe Asp Thr Leu Pro Gln Cys Asn Asp Cys Glu
        35                  40                  45

Val His Gly Gly Tyr Tyr Ile Gly Trp Ile Ser Val Gln Asp Gln Val
    50                  55                  60

Glu Ser Leu Val Lys Gln Gln Ala Ser Gln Tyr Pro Asp
65                  70                  75
```

ENZYME SYSTEM COMPRISING FERULIC ACID ESTERASE FROM ASPERGILLUS

The present invention relates to an enzyme system. In addition, the present invention relates to a nucleotide sequence coding for an enzyme useful in that system.

In addition, the present invention relates to the use of the enzyme system or the enzyme in food and feed, including the preparation of food and feed.

In particular, the enzyme system of the present invention comprises a ferulic acid esterase ("FAE"). More in particular, the present invention relates to a nucleotide sequence coding for an FAE and the FAE itself.

Cereal, fruit and vegetable cell walls largely consist of polysaccharide, the major components being pectin, cellulose and xyloglucan (see R. R. Selvendran and J. A. Robertson, IFR Report 1989). Numerous cell wall models have been proposed which attempt to incorporate the essential properties of strength and flexibility (e.g. see P. Albersheim, Sci. Am. 232, 81–95, 1975;, P. Albersheim, Plant Biochem. 3rd Edition (Bonner and Varner), Ac. Press, 1976; T. Hayashi, Ann. Rev. Plant Physiol. & Plant Mol. Biol., 40, 139–168, 1989).

The plant cell wall is a complex structure consisting of different polysaccharides. These polysaccharides comprise phenolic acid groups (i.e. the polysaccharides may be substituted with phenolic acids). A typical phenolic acid is ferulic acid ("FA"). In monocotyledons like wheat, FA is linked via an ester bond to the O5 of arabinose groups of arabinoxylans. In dicotyledons like beet, FA can be esterified to O2 of pectin arabinose and to O6 of the galactose residues.

Whilst it is known that FA can be oxidised by oxidases to form diferuloyl groups, which can create cross-linking of the polysaccharide chains, the physiological role of phenolic acid substituents, especially FA, in plant cell wall carbohydrate polymers is not clear.

However, it has been suggested that the formation of the diferuloyl groups may play a role in the control of cell wall growth in the plant and restrict cell wall digestion by microorganisms (Fry, S. C. (1983), Planta 157, 111–123; and Borneman, W. S. et al. (1990), Appl. Microbiol. Biotechnol. 33, 345–351).

Some microorganisms are known to exhibit FAE activity, which is believed to enable them to de-esterify arabinoxylans and pectins. In this regard, FAEs have been purified from *Aspergillus niger, Aspergillus awamori, Penicillium pinophilum* and Schizophyllum (Christov, L. P. and Prior, B. A. (1993), Enzyme Microb. Technol. 15, 460–475). An FAE from *Aspergillus niger* has been reported by Faulds and Williamson (Microbiol 1994 vol 140, pp779–787). Todate, no sequence data for FAEs obtained from a fungal origin have been reported.

It has now become common to eat food enriched with fibre, such as high fibre bread. This has led to production of different kinds of bread with fibre added, with the result that today much of the bread that is consumed is produced from whole wheat including the bran fraction. However, it is known that wheat bran has a negative effect on the gluten structure in a dough, and this effect cannot be explained solely by the lower gluten concentration in a dough supplemented with bran. By partly degrading the cell walls of wheat bran with alkaline hydrogen peroxide it is possible to improve the water binding capacity of wheat by a factor of 4 (Gould, J. M. et al. (1989), Cereal Chemistry 66(3), 201–205). This increase in water absorbing capacity can significantly improve the baking properties of wheat flour containing bran (Jasberg, B. K. et al. (1989), Cereal Chemistry 66(3), 205–209). It is known that wheat bran may contain up to 0.20% FA (w/w) and rye bran may contain up to 0.17% Fa (w/w) (Rybka, K.; Sitarski, J.; Raczynska-Bojanowska, K. (1993), Cereal Chemistry 70(1), 55–59) which may have a role in the strengthening of the plant cell wall. However, it is difficult to break down the cell wall structure and thereby improve the water binding capacity of the bran without using strongly oxidative chemicals.

The pentosan fraction of wheat flour plays a major role in dough development and in the baking of bread. This is due mainly to the water binding capacity of pentosans. It is well known that addition of pentosan modifying enzymes like xylanases can improve dough handling and the final bread. Nevertheless, it is still desirable to improve other qualities of dough—e.g. making a stronger dough.

It is also known that it is desirable to direct expression of a gene of interest ("GOI") in certain tissues of an organism—such as a filamentous fungus (such as *Aspergillus niger*) or even a plant crop. The resultant protein or enzyme of interest (commonly referred to as a "POI") may be useful for the organism itself. For example, it may be desirable to produce crop protein products with an optimised amino acid composition and so increase the nutritive value of a crop. For example, the crop may be made more useful as a food (e.g. for human consumption) or as a feed (e.g. for animal consumption).

In the alternative, it may be desirable to isolate the resultant protein or enzyme and then use the protein or enzyme to prepare, for example, food compositions or feed. In this regard, the resultant protein or enzyme can be a component of the food composition or feed or, alternatively, it can be used to prepare food compositions or feed, including altering the characteristics or appearance of food compositions.

The present invention seeks to provide an enzyme that can improve food and feed and the preparation of food and feed when used alone or more specifically when used in combination with at least one other protein or enzyme. In addition, preferably the present invention seeks to provide the enzyme by use of recombinant DNA techniques.

In the following commentary and unless the context is to the contrary, the reference to "enzyme" refers to the enzyme alone or in combination with at least one other protein or enzyme.

In particular the present invention seeks to provide an enzyme having FAE activity; preferably wherein the enzyme can be prepared in certain or specific cells or tissues, such as in just a specific cell or tissue, of an organism, typically a filamentous fungus, preferably of the genus Aspergillus, such as *Aspergillus niger*, or even a plant.

Also, the present invention seeks to provide a gene coding for the enzyme that can be expressed preferably in specific cells or tissues, such as in certain or specific cells or tissues, of an organism, typically a filamentous fungus, preferably of the genus Aspergillus, such as *Aspergillus niger*, or even a plant. Preferably, the enzyme after expression thereof is secreted into the surrounding medium from the host organism.

Furthermore, the present invention seeks to provide constructs, vectors, plasmids, cells, tissues, organs and organisms comprising the gene coding for the enzyme and, optionally, a suitable promoter, and methods of expressing the same, preferably in specific cells or tissues, such as expression in just a specific cell or tissue, of an organism, typically a filamentous fungus, preferably of the genus Aspergillus, or even a plant.

According to a first aspect of the present invention there is provided an enzyme system comprising a ferulic acid esterase ("FAE") and at least one protein or enzyme of interest ("POI"), wherein the FAE comprises any one or more of the sequences shown as SEQ. I.D. No. 1, SEQ. I.D. No. 2, SEQ. I.D. No. 3, SEQ. I.D. No. 6, or SEQ I.D. No. 7, or a variant, homologue or fragment thereof, preferably wherein if the FAE is genomic FAE and if just one POI is present then that POI is not a xylanase.

According to a second aspect of the present invention there is provided an enzyme system comprising FAE and at least one POI, wherein the FAE has the following characteristics
  a. a MW of either from about 29 kDa to about 36 kDa as measured on a SDS-Phastgel (10–15%) or about 30 kDa as measured by MALDI
  b. a pI value of about 3 to 4
  c. ferulic acid esterase activity
  d. a pH optimum of about 5 when MeFA is used as a substrate
  e. a temperature optimum of from about 50 to about 60° C. when MeFA is used as a substrate;
or a variant, homologue or fragment thereof;
wherein if the FAE is genomic FAE and if just one POI is present then that POI is not a xylanase.

According to a third aspect of the present invention there is provided an enzyme system comprising FAE and at least one POI, wherein the FAE has the following characteristics
  a. a MW of either from about 29 kDa to about 36 kDa as measured on a SDS-Phastgel (10–15%) or about 30 kDa as measured by MALDI
  b. a pI value of about 3 to 4
  c. ferulic acid esterase activity
  d. a pH optimum of about 5 when MeFA is used as a substrate
  e. a temperature optimum of from about 50 to about 60° C. when MeFA is used as a substrate
  f. any one or more of the sequences shown as SEQ. I.D. No. 1, SEQ. I.D. No. 2, SEQ. I.D. No. 3, SEQ. I.D. No. 6, or SEQ. I.D. No. 7;
or a variant, homologue or fragment thereof;
preferably wherein if the FAE is genomic FAE and if just one POI is present that POI is not a xylanase.

According to a fourth aspect of the present invention there is provided a recombinant enzyme that is obtainable from Aspergillus, wherein the enzyme has the following characteristics:
  a. a MW of from 29 kDa to 36 kDa as measured on a SDS-Phastgel (10–15%)
  b. a pI value of about 3 to 4
  c. ferulic acid esterase activity
  d. a pH optimum of about 5 when MeFA is used as a substrate
  e. a temperature optimum of from about 50 to about 60° C. when MeFA is used as a substrate
or a variant, homologue or fragment thereof.

According to a fifth aspect of the present invention there is provided a recombinant enzyme having ferulic acid esterase activity, the enzyme comprising any one or more of the sequences shown as SEQ. I.D. No. 1, SEQ. I.D. No. 2, SEQ. I.D. No. 3, SEQ. I.D. No. 6, or SEQ. I.D. No. 7, or a variant, homologue or fragment thereof.

According to a sixth aspect of the present invention there is provided a recombinant enzyme having ferulic acid esterase activity and encoded by a nucleotide sequence comprising any one or more of the sequences shown as SEQ. I.D. No. 4, SEQ. I.D. No. 5, or SEQ. I.D. No. 6, or a variant, homologue or fragment thereof or a sequence complementary thereto.

According to a seventh aspect of the present invention there is provided an amino acid sequence represented by any one of SEQ. I.D. No. 1, SEQ. I.D. No. 2, SEQ. I.D. No. 3, SEQ. I.D. No. 6, and SEQ. I.D. No. 7.

According to an eighth aspect of the present invention there is provided a nucleotide sequence coding for the FAE according to the present invention or the recombinant enzyme according to the present invention.

According to a ninth aspect of the present invention there is provided a nucleic acid sequence represented by any one of SEQ. I.D. No. 4, SEQ. I.D. No. 5, and SEQ. I.D. No. 6.

According to a tenth aspect of the present invention there is provided a nucleotide sequence comprising any one or more of the sequences shown as SEQ. I.D. No. 4, SEQ. I.D. No. 5, or SEQ. I.D. No. 6, or a variant, homologue or fragment thereof or a sequence complementary thereto.

According to an eleventh aspect of the present invention there is provided an internal sequence having the nucleotide sequence shown as SEQ. I.D. No. 6 or a variant, homologue or fragment thereof or a sequence complementary thereto.

According to a twelfth aspect of the present invention there is provided a N-terminal sequence having the sequence shown as SEQ. I.D. No. 1, or a variant, homologue or fragment thereof or a sequence complementary thereto.

According to a thirteenth aspect of the present invention there is provided a recombinant ferulic acid esterase enzyme, which is immunologically reactive with an antibody raised against a purified ferulic acid esterase enzyme which comprises at least one of the sequences shown as SEQ. I.D. No. 1, SEQ. I.D. No. 2, SEQ. I.D. No. 3, or SEQ. I.D. No. 7.

According to a fourteenth aspect of the present invention there is provided a combination of nucleotide sequences, the combination comprising a first construct comprising a gene coding for the enzyme according to the present invention operatively linked to a first promoter; and at least a second construct comprising a gene of interest ("GOI") operatively linked to a second promoter, wherein if the gene coding for the FAE is a genomic gene and if just one second construct is present then the GOI does not code for a xylanase.

According to a fifteenth aspect of the present invention there is provided a process of releasing a phenolic acid from a substrate comprising or containing phenolic acid subsituents, the process comprising treating the substrate with an enzyme system according to the present invention or a recombinant enzyme according to the present invention, preferably wherein the phenolic acid is at least FA.

Other aspects of the present invention include constructs, vectors, plasmids, cells, tissues, organs and transgenic organisms comprising or capable of expressing the aforementioned aspects of the present invention.

Further aspects of the present invention include methods of expressing or allowing expression or transforming any one of the nucleotide sequence, the construct, the plasmid, the vector, the cell, the tissue, the organ or the organism, as well as the products thereof.

Additional aspects of the present invention include expression of the gene coding for the enzyme in culture media such as a broth or in a transgenic organism.

Other aspects of the present invention include uses of the enzyme for preparing or treating plant material, foodstuffs, including animal feed. For example, the present invention covers any one of: the use of recombinant FAE to prepare a phenolic acid (preferably ferulic acid) for use as an anti-oxidant, preferably an in situ free anti-oxidant; the use of recombinant FAE to prepare a phenolic acid (preferably ferulic acid) to stabilise an oxidative agent (such as an oxidative enzyme), preferably to stabilise in situ an oxidative agent (such as an oxidative enzyme); the use of recombinant FAE to increase nutrient absorption, such as that of an animal feed; and the use of the recombinant FAE to prepare flavour precursors, such as vanillin.

Preferably, in the enzyme system the FAE is encoded by a nucleotide sequence comprising any one or more of the sequences shown as SEQ. I.D. No. 4, SEQ. I.D. No. 5, or SEQ. I.D. No. 6, or a variant, homologue or fragment thereof or a sequence complementary thereto.

Preferably in the enzyme system the POI is an oxidative enzyme.

Preferably in the enzyme system the POI is a polysaccharide modifying (e.g. degrading) enzyme.

Preferably in the enzyme system the polysaccharide modifying enzyme is any one or more of a xylanase, an arabinase, a glucanase, a pectinase, or a proteinase, preferably a xylanase, more preferably an endo-xylanase.

Preferably in the enzyme system the FAE is a recombinant FAE.

Preferably the nucleotide sequence is operatively linked to a promoter.

Preferably the transgenic organism is a fungus, preferably a filamentous fungus, more preferably a fungus of the family Aspergillus.

Preferably the transgenic organism is a yeast, which would then be useful in for example the baking industry.

Preferably the transgenic organism is a plant.

Preferably in the combination the gene coding for the enzyme according to the present invention comprises any one or more of the sequences shown as SEQ. I.D. No. 4, SEQ. I.D. No. 5, or SEQ. I.D. No. 6.

Preferably the GOI codes for a peroxidase, such as horse radish peroxidase (HRP).

Preferably the combination further comprises at least a third construct comprising a GOI operatively linked to a promoter.

Preferably the GOI of the third construct codes for a xylanase and/or GOX.

Preferably the substrate is or is derived from a plant, for example wheat such as bran or water insoluble pentosan (WIP), beet such as sugar beet, or corn such as corn cob.

Preferably the substrate comprises or is made from arabinoxylan, preferably when the substrate has been or is being treated with a xylanase.

Preferably the substrate is additionally treated with any one or more of a xylanase, an oxidative agent, or a peroxidase, such as HRP; wherein the oxidative agent can be an oxidative enzyme, and wherein the oxidative agent is preferably capable of generating hydrogen peroxide in situ, more preferably wherein the oxidative agent is GOX.

Preferably the substrate is or is used to form a food or feed.

Preferably the substrate is or is used to form a bakery product.

Preferably the substrate is or is used to form a dough.

Preferably the released phenolic acid (preferably ferulic acid) is subsequently used as a precursor to prepare vanillin.

Preferably the released phenolic acid (preferably ferulic acid) is subsequently used as an anti-oxidant, preferably as an in situ anti-oxidant.

Preferably the released phenolic acid (preferably ferulic acid) is subsequently used to stabilise an oxidative agent (such as an oxidative enzyme), preferably to stabilise in situ an oxidative agent (such as an oxidative enzyme).

Preferably, the enzyme is used in combination with any one of a glucanase, a proteinase, an acetyl esterase, a rhamnogalacturonase, an arabinase, a pectinase, a cellulase or a xylanase, preferably an endoxylanase.

Highly preferred embodiments of each of the aspects of the present invention do not include any one of the native enzyme or the native nucleotide sequence in its natural environment.

Preferably, in any one of the plasmid, the vector such as an expression vector or a transformation vector, the cell, the tissue, the organ, the organism or the transgenic organism, the gene coding for the enzyme is present in combination with a promoter.

Preferably the gene and the promoter are stably incorporated within the transgenic organism's genome.

Preferably the transgenic organism is a filamentous fungus, preferably of the genus Aspergillus, more preferably *Aspergillus niger*. The transgenic organism can even be a plant, such as a monocot or a dicot plant.

A highly preferred embodiment is therefore an enzyme system comprising recombinant FAE and at least one POI, wherein the FAE has the characteristics a. a MW of either from about 29 kDa to about 36 kDa as measured on a SDS-Phastgel (10–15%) or about 30 kDa as measured by MALDI b. a pI value of about 3 to 4 c. ferulic acid esterase activity d. a pH optimum of about 5 when MeFA is used as a substrate e. a temperature optimum of from about 50 to about 60° C. when MeFA is used as a substrate;

or a variant, homologue or fragment thereof; including the aforementioned uses thereof and processes using the same.

Another highly preferred embodiment is an enzyme system comprising recombinant FAE and at least one POI, wherein the FAE has the following characteristics a. a MW of either from about 29 kDa to about 36 kDa as measured on a SDS-Phastgel (10–15%) or about 30 kDa as measured by MALDI b. a pI value of about 3 to 4 c. ferulic acid esterase activity d. a pH optimum of about 5 when MeFA is used as a substrate e. a temperature optimum of from about 50 to about 60° C. when MeFA is used as a substrate f. any one or more of the sequences shown as SEQ. I.D. No. 1, SEQ. I.D. No. 2, SEQ. I.D. No. 3, or SEQ. I.D. No. 7;

or a variant, homologue or fragment thereof; including the aforementioned uses thereof and processes using the same.

The advantages of the present invention are that it provides a means for preparing an enzyme having ferulic acid esterase activity and a nucleotide sequence coding for the same. The enzyme is particularly useful for preparing food and feed, in particular dough and bakery products. In this regard, the enzyme of the present invention can do any one or more of: hydrolyse wheat, release species that can act as an anti-oxidant and preferably as an in situ anti-oxidant, release species that can act can stabilise an oxidising agent or enzyme and preferably stabilise in situ an oxidising agent or enzyme, and it can be used to increase nutrient absorption. The FAE of the present invention may even impair or prevent the formation of Form III horse radish peroxidase ("HRP") and preferably it can impair or prevent the in situ formation of Form III HRP.

Additional advantages are that transformed cells or organisms could prepare acceptable quantities of the desired compound or compounds which would be easily retrievable from the cells or organisms.

The enzyme system or the enzyme of the present invention can also enhance the value of beet or pectin from beet or other pectin containing material.

The enzyme system or the enzyme of the present invention may be added to animal feeds which are rich in arabinoxylans. When added to feeds for monogastic animals (e.g. poultry or swine) which contain cereals such as barley, wheat, corn, rye or oats or cereal by-products such as wheat bran or corn bran, the FAE enzyme of the present invention, particularly when used in combination with one or more other enzymes, significantly improves the break-down of plant cell walls which leads to better utilization of the plant nutrients by the animal. As a consequence, growth rate and/or feed conversion are improved. Moreover, arabinoxylan-degrading enzymes may also be used to reduce the viscosity of feed containing xylans. These arabinoxylan-degrading enzymes may be added beforehand to the feed if pre-soaking or wet diets are preferred.

Of particular benefit is the use of the enzyme according to the present invention in combination with a xylanase, especially an endoxylanase.

A possible further application for the enzyme according to the present invention is in the pulp and paper industry. The application of xylanases is often reported to be beneficial in the removal of lignins and terpenoids from the cellulose and hemicellulose residues of a hemiccllulose backbone, an essential step in the processing of wood, wood pulp or wood derivative product for the production of paper. The addition of the enzyme according to the present invention to the xylanase treatment step may therefore assist in the degradation of the polymer backbones and thus facilitate an improved, more efficient removal of both lignins and terpenoids.

The enzyme of the present invention is advantageous because it can release phenolic acids from substrates that contain or comprise phenolic acid substituents. This is of importance for many applications, especially increasing the nutritive value of feed. Examples of suitable substrates include polysaccharide based substrates, e.g. xylan polymers and pectin polymers, and oligomers, e.g. glyceride oligomers). The enzyme of the present invention may even release acetyl esters from substrates that contain or comprise acetyl ester substituents.

In particular, the enzyme of the present invention is advantageous because it can release FA from substrates that contain or comprise FA substituents.

The enzyme according to the present invention is also advantageous for wet-milling processes (i.e. enzymatic breakdown of cereals such as bran).

In addition a suitable enzyme system according to the present invention can affect the visco-elastic properties of ground cereals, such as dough, to ease the handling thereof and for example to get a higher volume of the bread.

In addition, a suitable enzyme system according to the present invention can reduce the viscosity of the feed in the intestine of the animals and so increase nutrient absorption and thus improve the quality of the feed.

In one aspect of the present invention, the enzyme system comprises at least FAE and a xylanase. This is particularly advantageous because the FAE and the xylanase have a synergistic effect with each other. In this regard, the FAE may increase the degradative effect of the xylanase, and the xylanase increases the degradative effect of the enzyme of the present invention. It is believed that the activity of the xylanase is increased because the enzyme of the present invention provides a polysaccharide substrate having fewer substituted groups.

In another aspect of the present invention the recombinant enzyme can be used in combination with other enzymes (such as a xylanase and/or other enzymes). When used with at least a xylanase, the enzyme is particularly useful for hydrolysing wheat bran. The enzyme can even increase the utilisation of feed. Furthermore the liberated FA can act as an antioxidant or it can stabilise peroxidase.

Other advantages of the present invention will be apparent from the following discussion.

The present invention therefore provides an enzyme having ferulic acid esterase activity wherein the enzyme can be prepared by recombinant DNA techniques, such as expression of a gene coding for the same in certain or specific cells or tissues, such as in just a specific cell or tissue, of an organism, typically a filamentous fungus, preferably of the genus Aspergillus, such as *Aspergillus niger*. The enzyme may even be prepared by a plant. The FAE may be used alone or in combination with one or more other proteins or enzymes.

In addition, the present invention provides a gene coding for the enzyme that can be expressed preferably in specific cells or tissues, such as in certain or specific cells or tissues, of an organism, typically a filamentous fungus, preferably of the genus Aspergillus, such as *Aspergillus niger*. The gene may even be expressed in a plant. At least one other GOI may be expressed in the same cells or tissues or organism.

Also, the present invention provides the expression of the gene coding for the enzyme by a promoter that is capable of directing expression of the gene, preferably in certain specific cells or tissues, such as in just a specific cell or tissue, of an organism, typically a filamentous fungus, preferably of the genus Aspergillus, such as *Aspergillus niger*, or even a plant. Preferably, the promoter is used in Aspergillus wherein the product encoded by the gene is secreted into the surrounding medium from the host organism.

The present invention also provides constructs, vectors, plasmids, cells, tissues, organs and organisms comprising the gene coding for the enzyme or enzyme system and, optionally, one or more promoters; and methods of expressing the same, preferably in specific cells or tissues, such as expression in just a specific cell or tissue, of an organism, typically a filamentous fungus, preferably of the genus Aspergillus, or even a plant.

The term "recombinant" is used in its normal sense. For example, the term "recombinant FAE" does not include FAE when prepared by expression of the genomic nucleotide sequence coding for FAE when that nucleotide sequence is in its natural environment. Thus, the term covers FAE when prepared by expression of a recombinant nucleotide sequence coding for the FAE when that nucleotide sequence is not in the natural environment for the genomic FAE coding sequence. The recombinant FAE can be used on its own or in combination with one or more other enzymes.

The terms "variant", "homologue" or "fragment" in relation to the enzyme include any substitution of, variation of, modification of, replacement of, deletion of or addition of one (or more) amino acid from or to the sequence providing the resultant amino acid sequence has ferulic acid esterase activity, preferably having at least the same activity of the enzyme comprising at least one of the sequences shown in the sequence listings (SEQ. I.D. No. 1, SEQ. I.D. No. 2, SEQ. I.D. No. 3, or SEQ. I.D. No. 7). In particular, the term "homologue" covers homology with respect to structure and/or function providing the resultant enzyme has ferulic acid esterase activity. With respect to sequence homology, preferably there is at least 75%, more preferably at least 85%, more preferably at least 90% homology to an enzyme comprising at least one of the sequences shown in the sequence listings (SEQ. I.D. No. 1, SEQ. I.D. No. 2, SEQ. I.D. No. 3, SEQ. I.D. No. 6, or SEQ. I.D. No. 7). More preferably there is at least 95%, more preferably at least 98%, homology to the sequences shown in the attached sequence listings. The same commentary is equally applicable to the terminal sequence.

The terms "variant", "homologue" or "fragment" in relation to the nucleotide sequence coding for the enzyme include any substitution of, variation of, modification of, replacement of, deletion of or addition of one (or more) nucleic acid from or to the sequence providing the resultant nucleotide sequence codes for an enzyme having ferulic acid esterase activity, preferably having at least the same activity of the enzyme comprising at least one of the sequences shown in the sequence listings (SEQ. I.D. No. 1, SEQ. I.D. No. 2, SEQ. I.D. No. 3, or SEQ. I.D. No. 7). In particular, the term "homologue" covers homology with respect to structure and/or function providing the resultant nucleotide sequence codes for an enzyme having ferulic acid esterase activity. With respect to sequence homology, preferably there is at least 75%, more preferably at least 85%, more preferably at least 90% homology to a nucleotide sequence comprising any one or more of the sequences shown as SEQ. I.D. No. 4, SEQ. I.D. No. 5, or SEQ. I.D. No. 6. More preferably there is at least 95%, more preferably at least 98%, homology to the sequences shown in the attached sequence listings.

The terms "variant", "homologue" or "fragment" in relation to the internal nucleotide sequence include any substitution of, variation of, modification of, replacement of, deletion of or addition of one (or more) nucleic acid from or to the sequence providing the resultant nucleotide sequence does not prevent expression of the gene coding for the FAE or the GOI in an expression system—such as the transformed cell or the transgenic organism according to the present invention. In particular, the term "homologue" covers homology with respect to structure and/or function. With respect to sequence homology, preferably there is at least 75%, more preferably at least 85%, more preferably at least 90% homology to SEQ ID NO. 6 shown in the attached sequence listings. More preferably there is at least 95%, more preferably at least 98%, homology to SEQ ID NO. 6 shown in the attached sequence listings.

The above terms are synonymous with allelic variations of the sequences.

The term "complementary" means that the present invention also covers nucleotide sequences that can hybridise to the nucleotide sequences.

The term "nucleotide" in relation to the present invention includes genomic DNA, cDNA, synthetic DNA, and RNA. Preferably it means DNA, more preferably it means cDNA.

The term "construct"—which is synonymous with terms such as "conjugate", "cassette" and "hybrid"—includes the gene coding for the present invention or a gene of interest ("GOI") directly or indirectly attached to an appropriate promoter. An example of an indirect attachment is the provision of a suitable spacer group such as an intron sequence, such as the Shl-intron or the ADH intron, intermediate the promoter and the coding gene, such as that coding for the enzyme of the present invention or a POI. The same is true for the term "fused" in relation to the present invention which includes direct or indirect attachment. In each case, it is highly preferred that the terms do not cover the coding gene in its natural environment.

The construct may even contain or express a marker which allows for the selection of the genetic construct in, for example, a filamentous fungus, preferably of the genus Aspergillus, such as *Aspergillus niger*, or plants, preferably cereals, such as corn, rice, barley etc., into which it has been transferred. Various markers exist which may be used, such as for example those encoding mannose-6-phosphate isomerase (especially for plants) or those markers that provide for antibiotic resistance—e.g. resistance to G418, hygromycin, bleomycin, kanamycin and gentamycin.

The term "vector" includes expression vectors and transformation vectors.

The term "expression system" includes a construct or vector or plasmid capable of in vivo or in vitro expression in a suitable host. The term also includes a suitable host expressing the GOI, such as the gene coding for the FAE, when present within the host as a construct, vector or plasmid or when integrated within the host's genomic structure.

The term "transformation vector" means a construct capable of being transferred from one species to another—such as from an *E.coli* plasmid to a filamentous fungus, preferably of the genus Aspergillus. It may even be a construct capable of being transferred from an *E.coli* plasmid to an Agrobacterium to a plant.

The terms "organ", "tissue" and "cell" include those components when in isolated form and when present within each other or within an organism.

The term "organism" in relation to the present invention includes any organism that could comprise the nucleotide sequence coding for the enzyme according to the present invention and/or products obtained therefrom, and/or wherein the nucleotide sequence according to the present invention can be expressed when present in the organism.

Preferably the organism is a filamentous fungus, preferably of the genus Aspergillus, more preferably *Aspergillus niger*.

The term "transgenic organism" in relation to the present invention includes any organism that comprises the nucleotide sequence coding for the enzyme according to the present invention and/or products obtained therefrom, and/or wherein the nucleotide sequence according to the present invention can be expressed within the organism. Preferably the nucleotide sequence is incorporated in the genome of the organism.

Preferably the transgenic organism is a filamentous fungus, preferably of the genus Aspergillus, more preferably *Aspergillus niger*.

Therefore, the transgenic organism of the present invention includes an organism comprising any one of, or combinations of, a nucleotide sequence coding for the enzyme according to the present invention, an expression system according to the present invention, a construct according to the present invention, a vector according to the present invention, a plasmid according to the present invention, a cell according to the present invention, a tissue according to the present invention or the products thereof. For example the transgenic organism can comprise a gene coding for the enzyme of the present invention, preferably an exogenous nucleotide sequence, under the control of a promoter.

The term "promoter" is used in the normal sense of the art, e.g. an RNA polymerase binding site in the Jacob-Monod theory of gene expression.

In one aspect, the nucleotide sequence according to the present invention is under the control of a promoter that allows expression of the nucleotide sequence. The promoter may be a cell or tissue specific promoter. If, for example, the organism is a plant then the promoter can be one that affects expression of the nucleotide sequence in any one or more of stem, sprout, root and leaf tissues. By way of example, the promoter for the nucleotide sequence of the present invention can be the α-Amy 1 promoter (otherwise known as the Amy 1 promoter, the Amy 637 promoter or the α-Amy 637 promoter) as described in our co-pending UK patent application Ser. No. 9421292.5 filed Oct. 21, 1994. Alternatively, the promoter for the nucleotide sequence of the present invention can be the α-Amy 3 promoter (otherwise known as the Amy 3 promoter, the Amy 351 promoter or the α-Amy 351 promoter) as described in our co-pending UK patent application Ser. No. 9421286.7 filed Oct. 21, 1994.

The promoter could additionally include features to ensure or to increase expression in a suitable host. For example, the features can be conserved regions such as a Pribnow Box or a TATA box. The promoters may even contain other sequences to affect (such as to maintain, enhance, decrease) the levels of expression of the gene coding for the enzyme of the present invention. For example, suitable other sequences include the Sh1-intron or an ADH intron. Other sequences include inducible elements—such as temperature, chemical, light or stress inducible elements. Also, suitable elements to enhance transcription or translation may be present. An example of the latter element is the TMV 5' signal sequence (see Sleat Gene 217 [1987] 217–225; and Dawson Plant Mol. Biol. 23 [1993] 97).

In addition the present invention also encompasses combinations of promoters and/or nucleotide sequences coding for proteins or enzymes and/or elements. For example, the present invention encompasses the combination of a promoter operatively linked to a GOI, and a promoter operatively linked to a gene coding for the enzyme of the present invention, wherein the promoters can be the same or different. Each promoter may be a tissue specific promoter.

The present invention also encompasses the use of promoters to express a nucleotide sequence coding for the enzyme according to the present invention, wherein a part of the promoter is inactivated but wherein the promoter can still function as a promoter. Partial inactivation of a promoter in some instances is advantageous. In particular, with the Amy 351 promoter mentioned earlier it is possible to inactivate a part of it so that the partially inactivated promoter expresses the gene coding for the enzyme of the present invention in a more specific manner such as in just one specific tissue type or organ. The term "inactivated" means partial inactivation in the sense that the expression pattern of the promoter is modified but wherein the partially inactivated promoter still functions as a promoter. However, as mentioned above, the modified promoter is capable of expressing a gene coding for the enzyme of the present invention in at least one (but not all) specific tissue of the original promoter. Examples of partial inactivation include altering the folding pattern of the promoter sequence, or binding species to parts of the nucleotide sequence, so that a part of the nucleotide sequence is not recognised by, for example, RNA polymerase. Another, and preferable, way of partially inactivating the promoter is to truncate it to form fragments thereof. Another way would be to mutate at least a part of the sequence so that the RNA polymerase can not bind to that part or another part. Another modification is to mutate the binding sites for regulatory proteins for example the CreA protein known from filamentous fungi to exert carbon catabolite repression, and thus abolish the catabolite repression of the native promoter.

As indicated above, the gene according to the present invention can be expressed in combination (not necessarily at the same time) with an additional construct, wherein the additional construct comprises a GOI and a promoter. Thus the present invention also provides a combination of constructs comprising a first construct comprising the gene coding for the enzyme according to the present invention operatively linked to a first promoter; and a second construct comprising a GOI operatively linked to a second promoter (which need not be the same as the first promoter). With this aspect of the present invention the combination of constructs may be present in the same vector, plasmid, cells, tissue, organ or organism. This aspect of the present invention also covers methods of expressing the same, preferably in specific cells or tissues, such as expression in just a specific cell or tissue, of an organism, typically a filamentous fungus, preferably of the genus Aspergillus, or even a plant. Likewise with this aspect of the present invention the second construct does not cover the natural combination of the gene coding for an enzyme ordinarily associated with a wild type gene promoter and when they are both in their natural environment.

The term "GOI" with reference to this aspect of the present invention means any gene of interest. A GOI can be any nucleotide that is either foreign or natural to the organism (e.g. filamentous fungus, preferably of the genus Aspergillus, or a plant) in question. The product of the GOI is the POI.

Typical examples of a GOI include genes encoding for other proteins or enzymes that modify metabolic and catabolic processes. The GOI may code for an agent for introducing or increasing pathogen resistance. The GOI may even be an antisense construct for modifying the expression of natural transcripts present in the relevant tissues.

The GOI may even code for a non-natural protein of a filamentous fungus, preferably of the genus Aspergillus, or a compound that is of benefit to animals or humans. For example, the GOI could code for a pharmaceutically active protein or enzyme such as any one of the therapeutic compounds insulin, interferon, human serum albumin, human growth factor and blood clotting factors.

The GOI may even code for a protein giving additional nutritional value to a food or feed or crop. Typical examples include plant proteins that can inhibit the formation of anti-nutritive factors and plant proteins that have a more desirable amino acid composition (e.g. a higher lysine content than a non-transgenic plant). The GOI may even code for an enzyme that can be used in food processing such as xylanases and α-galactosidase. The GOI can be a gene encoding for any one of a pest toxin, an antisense transcript such as that for α-amylase, a protease or a glucanase.

The GOI can be the nucleotide sequence coding for the arabinofuranosidase enzyme which is the subject of our co-pending UK patent application Ser. No. 9505479.7. The GOI can be the nucleotide sequence coding for the glucanase enzyme which is the subject of our co-pending UK patent application Ser. No. 9505475.5. The GOI can be the nucleotide sequence coding for the α-amylase enzyme which is the subject of our co-pending UK patent application Ser. No. 9413439.2. The GOI can be the nucleotide sequence coding for the α-amylase enzyme which is the subject of our co-pending UK patent application Ser. No. 9421290.9. The GOI can be any of the nucleotide sequences coding for the α-glucan lyase enzyme which are described in our co-pending PCT patent application PCT/EP94/03397.

In one aspect the GOI can even be a nucleotide sequence coding for the enzyme according to the present invention but when operatively linked to a different promoter.

Preferred GOIs include one or more of a xylanase, an arabinase, an acetyl esterase, a rhamnogalacturonase, a glucanase, a pectinase, or another carbohydrate modifying enzyme or proteinase.

The host organism can be a prokaryotic or a eukaryotic organism. Examples of suitable prokaryotic hosts include *E. coli* and *Bacillus subtilis*. Teachings on the transformation of prokaryotic hosts is well documented in the art, for example see Sambrook et al (infra). If a prokaryotic host is used then the GOI, such as the gene coding for the FAE, may need to be suitably modified before transformation—such as by removal of introns.

As mentioned above, a preferred host organism is of the genus Aspergillus, such as *Aspergillus niger*. The transgenic Aspergillus according to the present invention can be prepared by following the teachings of Rambosek, J. and Leach, J. 1987 (Recombinant DNA in filamentous fungi: Progress and Prospects. CRC Crit. Rev. Biotechnol. 6:357–393), Davis R. W. 1994 (Heterologous gene expression and protein secretion in Aspergillus. In: Martinelli S. D., Kinghom J. R.( Editors) Aspergillus: 50 years on. Progress in industrial microbiology vol 29. Elsevier Amsterdam 1994. pp 525–560), Ballance, D. J. 1991 (Transformation systems for Filamentous Fungi and an Overview of Fungal Gene structure. In: Leong,S. A., Berka R. M. (Editors) Molecular Industrial Mycology. Systems and Applications for Filamentous Fungi. Marcel Dekker Inc. New York 1991. pp 1–29) and Turner G. 1994 (Vectors for genetic manipulation. In: Martinelli S. D., Kinghom J. R.( Editors) Aspergillus: 50 years on. Progress in industrial microbiology vol 29. Elsevier Amsterdam 1994. pp. 641–666). However, the following commentary provides a summary of those teachings for producing transgenic Aspergillus according to the present invention.

Filamentous fungi have been widely used in industry for production of organic compounds and enzymes. Traditional japanese koji and soy fermentations have used Aspergillus sp for hundreds of years. In this century *Aspergillus niger* has been used for production of organic acids particular citric acid and for production of various enzymes for use in industry.

There are two major reasons for that filamentous fungi have been so widely used in industry. First filamentous fungi can produce high amounts of extracellular products, for example enzymes and organic compounds such as antibiotics or organic acids. Second filamentous fungi can grow on low cost substrates such as grains, bran, beet pulp etc. The same reasons have made filamentous fungi attractive organisms as hosts for heterologous gene expression according to the present invention.

In order to prepare the transgenic Aspergillus, expression constructs are prepared by inserting the GOI (such as the gene coding for the enzyme of the present invention) into a construct designed for expression in filamentous fungi. In this regard, several types of constructs used for heterologous gene expression have been developed. The constructs will contain a promoter which is active in fungi. Examples of promoters include a fungal promoter for a highly expressed extracellular enzyme, such as the glucoamylase promoter or the α-amylase promoter. The GOI can be fused to a signal sequence which directs the protein encoded by the GOI to be secreted. Usually a signal sequence of fungal origin is used. A terminator active in fungi ends the expression system.

Another type of expression system has been developed in fungi where the GOI (such as the gene coding for the enzyme of the present invention) is fused to a smaller or a larger part of a fungal gene encoding a stable protein. This can stabilize the protein encoded by the GOI. In such a system a cleavage site, recognized by a specific protease, can be introduced between the fungal protein and the protein encoded by the GOI, so the produced fusion protein can be cleaved at this position by the specific protease thus liberating the protein or enzyme encoded by the GOI—i.e. the POI. By way of example, one can introduce a site which is recognized by a KEX-2 like peptidase found in at least some Aspergilli. Such a fusion leads to cleavage in vivo resulting in protection of the POI and production of POI and not a larger fusion protein.

Heterologous expression in Aspergillus has been reported for several genes coding for bacterial, fungal, vertebrate and plant proteins. The proteins can be deposited intracellularly if the GOI is not fused to a signal sequence. Such proteins will accumulate in the cytoplasm and will usually not be glycosylated which can be an advantage for some bacterial proteins. If the GOI is equipped with a signal sequence the protein will accumulate extracellulary.

With regard to product stability and host strain modifications, some heterologous proteins are not very stable when they are secreted into the culture fluid of fungi. Most fungi produce several extracellular proteases which degrade heterologous proteins. To avoid this problem special fungal strains with reduced protease production have been used as hosts for heterologous production.

For the transformation of filamentous fungi, several transformation protocols have been developed for many filamentous fungi. Many of them are based on preparation of protoplasts and introduction of DNA into the protoplasts using PEG and $Ca^{2+}$ ions. The transformed protoplasts then regenerate and the transformed fungi are selected using various selective markers. Among the markers used for transformation are a number of auxotrophic markers such as argB, trpC, niaD and pyrG, antibiotic resistance markers such as benomyl resistance, hygromycin resistance and phleomycin resistance. A very common used transformation marker is the amdS gene of *A. nidulans* which in high copy number allows the fungus to grow with acrylamide as the sole nitrogen source.

In another preferred embodiment the transgenic organism is a yeast. In this regard, yeast have been widely used as a vehicle for heterologous gene expression. The species *Saccharomyces cerevisiae* has a long history of industrial use, including use for heterologous gene expression. Expression of heterologous genes in *Saccharomyces cerevisiae* has been reviewed by Goodey et al (1987, Yeast Biotechnology, D R Berry et al, eds, pp 401–429, Allen and Unwin, London) and by King et al (1989, Molecular and Cell Biology of Yeasts, E F Walton and G T Yarronton, eds, pp 107–133, Blackie, Glasgow).

For several reasons *Saccharomyces cerevisiae* is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae*.

An additional advantage is that yeasts are capable of post-translational modifications of proteins and thereby have the potential for glycosylation and/or secretion of heterologous gene products into the growth medium. A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

Also, yeasts are known to secrete very few proteins into the culture medium. This makes yeast a very attractive host for expression of heterologous genes, since secretable gene products can easily be recovered and purified.

Several types of yeast vectors are available, including integrative vectors, which require recombination with the host genome for their maintenance, and autonomously replicating plasmid vectors.

The glycosylation of enzymes expressed in yeast may increase heat stability of the enzyme. Enhancing the heat stability of the enzyme according to the present invention would therefore make the enzyme suitable for use in the baking industry and for use in the preparation of animal feed, e.g. chicken feed.

In order to prepare the transgenic Saccharomyces, expression constructs are prepared by inserting a GOI (such as a gene coding for the enzyme of the present invention) into a construct designed for expression in yeast. Several types of constructs used for heterologous expression have been developed. The constructs contain a promoter active in yeast fused to the GOI, usually a promoter of yeast origin, such as the GAL1 promoter, is used. The GOI can be fused to a signal sequence which directs the protein encoded by the GOI to be secreted. Usually a signal sequence of yeast origin, such as the sequence encoding the SUC2 signal peptide, is used. A terminator active in yeast ends the expression system.

Heterologous expression in yeast has been reported for several genes. The gene products can be glycosylated which is advantageous for some enzymes intended for specific application where heat tolerance is desirable. The proteins can be deposited intracellularly if the GOI is not fused to a signal sequence, or they can be secreted extracelluarly if the GOI is equipped with a signal sequence.

For the transformation of yeast several transformation protocols have been developed. The transgenic Saccharomyces according to the present invention can be prepared by following the teachings of Hinnen et al (1978, Proceedings of the National Academy of Sciences of the USA 75, 1929); Beggs, J D (1978, Nature, London, 275, 104); and Ito, H et al (1983, J Bacteriology 153, 163–168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, eg G418.

Even though the enzyme according to the present invention and the nucleotide sequence coding for same are not disclosed in EP-B-0470145 and CA-A-2006454, those two documents do provide some useful background commentary on the types of techniques that may be employed to prepare transgenic plants according to the present invention. Some of these background teachings are now included in the following commentary.

The basic principle in the construction of genetically modified plants is to insert genetic information in the plant genome so as to obtain a stable maintenance of the inserted genetic material.

Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205–225) and Christou (Agro-Food-Industry Hi-Tech March/April 1994 17–27).

Thus, in one aspect, the present invention relates to a vector system which carries a nucleotide sequence or construct according to the present invention and which is capable of introducing the nucleotide sequence or construct into the genome of an organism, such as a plant.

The vector system may comprise one vector, but it can comprise two vectors. In the case of two vectors, the vector system is normally referred to as a binary vector system. Binary vector systems are described in further detail in Gynheung An et al. (1980), Binary Vectors, *Plant Molecular Biology Manual* A3, 1–19.

One extensively employed system for transformation of plant cells with a given promoter or nucleotide sequence or construct is based on the use of a Ti plasmid from *Agrobacterium tumefaciens* or a Ri plasmid from *Agrobacterium rhizogenes* An et al. (1986), *Plant Physiol.* 81, 301–305 and Butcher D. N. et al. (1980), *Tissue Culture Methods for Plant Pathologists*, eds.: D. S. Ingrams and J. P. Helgeson, 203–208.

Several different Ti and Ri plasmids have been constructed which are suitable for the construction of the plant or plant cell constructs described above. A non-limiting example of such a Ti plasmid is pGV3850.

The nucleotide sequence or construct of the present invention should preferably be inserted into the Ti-plasmid between the terminal sequences of the T-DNA or adjacent a T-DNA sequence so as to avoid disruption of the sequences immediately surrounding the T-DNA borders, as at least one of these regions appear to be essential for insertion of modified T-DNA into the plant genome.

As will be understood from the above explanation, if the organism is a plant, then the vector system of the present invention is preferably one which contains the sequences necessary to infect the plant (e.g. the vir region) and at least one border part of a T-DNA sequence, the border part being located on the same vector as the genetic construct.

Furthermore, the vector system is preferably an *Agrobacterium tumefaciens* Ti-plasmid or an *Agrobacterium rhizogenes* Ri-plasmid or a derivative thereof. As these plasmids are well-known and widely employed in the construction of transgenic plants, many vector systems exist which are based on these plasmids or derivatives thereof.

In the construction of a transgenic plant the promoter or nucleotide sequence or construct of the present invention may be first constructed in a microorganism in which the vector can replicate and which is easy to manipulate before insertion into the plant. An example of a useful microorganism is *E. coli*, but other microorganisms having the above properties may be used. When a vector of a vector system as defined above has been constructed in *E. coli*, it is transferred, if necessary, into a suitable Agrobacterium strain, e.g. *Agrobacterium tumefaciens*. The Ti-plasmid harbouring the nucleotide sequence or construct of the present invention is thus preferably transferred into a suitable Agrobacterium strain, e.g. *A. tumefaciens*, so as to obtain an Agrobacterium cell harbouring the promoter or nucleotide sequence or construct of the present invention, which DNA is subsequently transferred into the plant cell to be modified.

If, for example, for the transformation the Ti- or Ri-plasmid of the plant cells is used, at least the right boundary and often however the right and the left boundary of the Ti- and Ri-plasmid T-DNA, as flanking areas of the introduced genes, can be connected. The use of T-DNA for the transformation of plant cells has been intensively studied and is described in EP-A-120516; Hoekema, in: The Binary Plant Vector System Offset-drukkerij Kanters B. B., Alblasserdam, 1985, Chapter V; Fraley, et al., Crit. Rev. Plant Sci., 4:1–46; and An et al., EMBO J. (1985) 4:277–284.

Direct infection of plant tissues by Agrobacterium is a simple technique which has been widely employed and which is described in Butcher D. N. et al. (1980), *Tissue Culture Methods for Plant Pathologists*, eds.: D. S. Ingrams and J. P. Helgeson, 203–208. For further teachings on this topic see Potrykus (Annu Rev Plant Physiol Plant Mol Biol [1991] 42:205–225) and Christou (Agro-Food-Industry Hi-Tech March/April 1994 17–27). With this technique, infection of a plant may be done on a certain part or tissue of the plant, i.e. on a part of a leaf, a root, a stem or another part of the plant.

Typically, with direct infection of plant tissues by Agrobacterium carrying the GOI (such as the gene coding for the enzyme according to the present invention) and, optionally, a promoter, a plant to be infected is wounded, e.g. by cutting the plant with a razor or puncturing the plant with a needle or rubbing the plant with an abrasive. The wound is then inoculated with the Agrobacterium. The inoculated plant or plant part is then grown on a suitable culture medium and allowed to develop into mature plants.

When plant cells are constructed, these cells may be grown and maintained in accordance with well-known tissue culturing methods such as by culturing the cells in a suitable culture medium supplied with the necessary growth factors such as amino acids, plant hormones, vitamins, etc.

Regeneration of the transformed cells into genetically modified plants may be accomplished using known methods for the regeneration of plants from cell or tissue cultures, for example by selecting transformed shoots using an antibiotic and by subculturing the shoots on a medium containing the appropriate nutrients, plant hormones, etc.

Further teachings on plant transformation may be found in EP-A-0449375.

As reported in CA-A-2006454, a large amount of cloning vectors are available which contain a replication system in *E. coli* and a marker which allows a selection of the transformed cells. The vectors contain for example pBR 322, pUC series, M13 mp series, pACYC 184 etc. In this way, the nucleotide or construct of the present invention can be introduced into a suitable restriction position in the vector. The contained plasmid is then used for the transformation in *E.coli*. The *E.coli* cells are cultivated in a suitable nutrient medium and then harvested and lysed. The plasmid is then recovered. As a method of analysis there is generally used sequence analysis, restriction analysis, electrophoresis and further biochemical-molecular biological methods. After each manipulation, the used DNA sequence can be restricted and connected with the next DNA sequence. Each sequence can be cloned in the same or different plasmid.

After the introduction the nucleotide sequence or construct according to the present invention in the plants the presence and/or insertion of further DNA sequences may be necessary—such as to create combination systems as outlined above (e.g. an organism comprising a combination of constructs).

The following samples of Bacteriophage lamda EMBL4 have been deposited in accordance with the Budapest Treaty at the recognised depositary The National Collections of Industrial and Marine Bacteria Limited (NCIMB) at 23 St Machar Drive, Aberdeen, Scotland, AB2 1RY, United Kingdom, on May 18, 1995: NCIMB 40733 (which refers to Phage 1 as described herein); and NCIMB 40734 (which refers to Phage 2 as described herein).

Construction of a functional gene from the deposits

From the isolated phages the complete clone can be assembled following extraction of DNA from Phage 1 and Phage 2 by the procedure described in Sambrook et al (Sambrook et al. in Molecular Cloning: A Laboratory Manual, 2nd edition, 1989, Cold Spring Harbor Laboratory Press). In this regard, Phage 1 DNA is digested with SalI and PstI, and a fragment of approximately 0.5 kbp is purified. Phage 2 DNA is digested with PstI and HindIII and a fragment of approximately 1.5 kbp is purified. The two fragments are inserted into pBluescript SK+ (Stratagene, La Jolla, US) digested with SalI and HindIII (Yanisch-Perron et al. (1985), Gene 33, 103–109) or into another suitable vector. The resultant plasmid contains the functional FAE gene. Standard molecular genetics techniques can be performed according to Sambrook et al (ibid).

Thus, a highly preferred embodiment is an enzyme system comprising recombinant FAE and at least one POI, wherein the FAE has the following characteristics a. a MW of either from about 29 kDa to about 36 kDa as measured on a SDS-Phastgel (10–15%) or about 30 kDa as measured by MALDI b. a pI value of about 3 to 4 c. ferulic acid esterase activity d. a pH optimum of about 5 when MeFA is used as a substrate e. a temperature optimum of from about 50 to about 60° C. when MeFA is used as a substrate;

f. the FAE is expressable by the FAE coding sequences of NCIMB 40733 or NCIMB 40734;

or a variant, homologue or fragment thereof; including the aforementioned uses thereof and processes using the same.

Another highly preferred embodiment is an enzyme system comprising recombinant FAE and at least one POI, wherein the FAE has the following characteristics a. a MW of either from about 29 kDa to about 36 kDa as measured on a SDS-Phastgel (10–15%) or about 30 kDa as measured by MALDI b. a pI value of about3 to 4 c. ferulic acid esterase activity d. a pH optimum of about 5 when MeFA is used as a substrate e. a temperature optimum of from about 50 to about 60° C. when MeFA is used as a substrate f. any one or more of the sequences shown as SEQ. I.D. No. 1, SEQ. I.D. No. 2, SEQ. I.D. No. 3, or SEQ. I.D. No. 7;

g. the FAE is expressable by the FAE coding sequences of NCIMB 40733 and NCIMB 40734;

or a variant, homologue or fragment thereof; including the aforementioned uses thereof and processes using the same.

In summation, the present invention therefore provides an enzyme having ferulic acid esterase activity and a nucleotide sequence coding for the same. In addition the present invention provides an enzyme system comprising FAE.

The present invention will now be described by way of example.

A. EXPERIMENTAL

1. Methyl Ferulate

1.1 Preparation of methyl ferulate

The activity of the FAE according to the present invention was studied using inter alia methyl ferulate ("MeFA").

MeFA was prepared according to the teachings of Fry (Fry, S. C. (1982), Biochem. J. 203, 493–504). In this regard, 500 mg of FA (obtained from Sigma) were dissolved in 20 ml methanol. 0.8 ml concentrated $H_2SO_4$ was added, and the sample was incubated for 2 hours at 50° C. Sodium-phosphate buffer, 0.4M, pH 8.3 was added to a total volume of 100 ml. MeFA was extracted in 3×10 ml of diethyl ether—which was evaporated to obtain pure MeFA. The identity of the substrate was confirmed by NMR and MS. MeFA is an ideal substrate for FAE as it is easily handled.

1.2 Measurement of FAE activity using MeFA

Enzyme activity on MeFA was measured by incubating 75 µl of an enzyme solution with 300 µl of MeFA in acetate buffer, 50 mM, pH 5 (2 mg MeFA per ml) at 50° C. After 0, 2, 4, 6, 8 and 10 minutes, 50 µl samples were taken out and added to 2.5 ml glycine buffer (10 mM, pH 10) in order to stop the reaction. The absorbance at 325 nm was determined, and absorbance was plotted against time. The activity was calculated from the slope of the curve using an extinction coefficient of 22900 $M^{-1}$ $cm^{-1}$ for FA at pH 10. FAE units in the following studies refer to amount of FA released from MeFA in umol/hour/ml.

2. Wheat Pentosan

2.1 Preparation of wheat pentosan

The activity of the FAE according to the present invention was studied using inter alia water insoluble wheat pentosan.

Water insoluble wheat pentosan (WIP) was prepared from wheat flour by washing out the starch, subsequently treating the remanence with amylase, and then washing the remanence with water. Precipitation of the high-molecular weight fraction with acetone was then carried out and that fraction (i.e. the high molecular weight fraction) was dried (Rouau, X.; Moreau, D. (1993), Cereal Chem. 70(6), 626–632).

2.2 Measurement of FAE activity using WIP 10 ml sodium acetate buffer, 100 mM, pH 4.8 was added to 0.1 g of WIP. The suspension was then heated to boiling and then cooled to 50° C. 1 ml of FAE solution was then added and the sample was incubated at 50° C. for one hour. The reaction was stopped by boiling the sample for 5 minutes. After filtration, the amount of liberated FA in the sample was measured by reverse phase HPLC on a Spherisorb C8 column (Merck) equilibrated with 0.3% acetic acid. FA was eluted with a gradient of 80% methanol (in 0.3% acetic acid) and was detected by diode array at 325 nm.

3. Determination of FA levels

The contents of FA in different plant cell preparations was determined as described by Tenkanen et al (Tenkanen et al. (1991), J. Biotechnol. 18, 69–84). In this regard, 50–100 mg of the samples were incubated overnight with 3 ml 0.1M NaOH. The samples were centrifuged and diluted in 25% MeOH and then analysed on a Nucleosil C18 column with 25% McOH containing 5 mM TBAHS (tetrabutylammoniumhydrogensulphate) and 10 mM $KH_2PO_4$ buffer as the mobile phase. FA was detected at 310 nm.

4. Xylanase

4.1 Preparation of xylanase

Xylanase (xylanase-1) was purified from GRINDAMYL S100™ (which is supplied by and is a trade mark of Danisco A/S) by use of anion exchange and gel filtration.

4.2 Measurement of xylanase activity

Activity was measured using azurine cross-linked birchwood xylan in the form of Xylazyme Tablets (from Megazyme, Australia) using the manufacturer's recommended conditions. In this regard, 1 ml Na-acetate buffer, 200 mM, pH 5 is preheated with 50, 75 and 100 µl enzyme solution respectively. The reaction is initiated by adding a Xylazyme tablet to each test tube. After 10 minutes at 40° C. the reaction is terminated by adding 10 ml of stop solution. The samples are filtered and the absorbance at 590 nm is determined. GRINDAMYL S100™ was used as a standard with a defined activity of 10,000 units per gram.

B. PURIFICATION AND CHARATE RISATION OF FAB

1. Purification of FAE

FAE was purified from PEKTOLASE™ CA (which is supplied by and is a trade mark of Danisco A/S). In this regard, 15 ml of PEKTOLASE™ CA was diluted twice with MES-buffer, 50 mM, pH 6.8, and applied to an anion exchange column (DEAE-Sepharose FF, 25×200), equilibrated with the MES buffer. FAE was eluted with a linear gradient of 2 l of MES buffer with 0.6M NaCl (flow 100 ml/hour). Of the fractions screened for FAE activity with MeFA—one major peak was found. FAE containing fractions were then pooled, and 1.5M $(NH_4)_2SO_4$ was added. The sample was then applied to a Phenyl-Sepharose HiLoad column (26 mm×100 mm) equilibrated with sodium phosphate buffer, 50 mM, pH 6.8, containing 1.5M $(NH_4)_2SO_4$. FAE was eluted with a linear gradient of sodium phosphate buffer (flow 5 ml/min, 600 ml gradient). FAE containing fractions were then pooled, and the sample was applied to a gel filtration column, Sephacryl HiLoad (16 mm×60 mm) equilibrated with Tris buffer, 50 mM, pH 7 with 0.1M NaCl (flow 0.66 ml/min). FAE containing fractions were then pooled, buffer was then changed to sodium acetate buffer, 100 mM, pH 5.0, and the sample was applied to a MonoQ HR 5/5 anion exchange column equilibrated with the acetate buffer. FAE was eluted with a linear gradient of 30 ml acetate buffer with 0.5M NaCl (flow 1 ml/min).

2. MW characterisation of FAE

The MW of FAE was determined by MALDI (matrix assisted desorption mass spectrometry) and it was found to be approximately 29.570 kDa. The mass spectra showed that the enzyme is glycosylated with a complex, heterogenous glyco-structure.

Using SDS-PAGE analysis, purified samples had a MW of about from 29–36 kDa, typically 29–32 kDa or 36 kDa, on a SDS-Phastgel (10–15%). On a tris-glycine gel, 4–12%, the molecular weights were approximately 3 kDa lower. It is believed that the slight differences in the MW of the purified samples are attributible to proteolytical modification of the FAE during its purification. An alternative explanation may be as a result of the fact that the enzyme is glycosylated with a complex glyco-structure that is very heterogenous.

3. Amino acid sequencing of the N-Terminal of FAE and FAE peptides

Amino acid sequences were determined according to traditional procedures using modifications described by Stone and Williams (ibid). In this regard, the enzyme was digested with either lysC endoproteinase (sequencing grade from Boehringer Mannheim), V8 protease (Sigma) or CNBr. For example, lysC digestion was as follows: A purified, desalted sample of FAE (60 μg protein) was freeze dried. This material was re-dissolved in 50 μl $NH_4HCO_3$, 0.4M and urea, 8M, pH 8.1 and left under $N_2$ for 5 minutes at 50° C. 5 μl DTT, 50 mM was added and the sample was again incubated at 50° C. under $N_2$. Then, 5 μl iodoacetamide, 100 mM was added and the sample was incubated at room temperature for 15 minutes. 136 μl $H_2O$ and 4 μg endoproteinase lys-C were then added and the sample was incubated over night at 37° C. under $N_2$. The enzyme digestion was stopped by freezing the sample. The sample was applied to a reverse phase column (C18, Vydac) equilibrated with 0.1% TFA in water, and peptides were separated by eluting with 0.1% TFA in acetonitrile in a 10–40% gradient. Individual peptides were applied to micro-TFA filters and analysed on an Applied Biosystems Amino Acid Sequencer, model 476 A. A total of 132 amino acids were sequenced. The sequence information is shown in SEQ I.D. No.s 1–3.

4. pI characterisation of FAE

The FAE enzyme has a pI of about 3–4 (on a IEF 3–9 Phastsystem Gel, Pharmacia).

5. pH optimum characterisation of FAE

The FAE enzyme has a pH optimum at pH 5 (measured in 50 mM acetate and Tris buffers with an incubation of 15 min.) when MeFA is used as a substrate.

6. Temperature optimum characterisation of FAE

The FAE enzyme has a temperature optimum is 50–60° C. (at pH 5 in 50 mM acetate buffer, incubation time 15 min) when MeFA is used as a substrate.

7. Enzymatic activity characterisation of FAE

As mentioned above, the FAE enzyme was isolated based on its activity on MeFA. In this regard, the enzyme was investigated to determine its ability to release FA from a WIP fraction containing 0.6 % FA (w/w). Further studies were done whereby xylanase was also added. The results are shown below in Table 1.

TABLE 1

FAE activity on water insoluble pentosan from wheat flour

| Amount of xylanase added (U) | Amount of FAE added (U) | Released FA (ng/ml) |
|---|---|---|
|  | 0.0018 | 12 |
|  | 0.018 | 37 |
|  | 0.18 | 277 |
| 0.45 |  | 0 |
| 0.45 | 0.0018 | 19 |
| 0.45 | 0.018 | 102 |
| 0.45 | 0.18 | 721 |

As shown from the data in Table 1, the FAE of the present invention releases FA from WIP.

In addition, the results show that addition of xylanase increases the amount of FA released. These results indicate that the FAE enzyme has a higher activity on arabinoxylans-oligomers than on polymers.

C. ISOLATON OF THE FAE GENE

1. Construction of a genomic library of Aspergillus niger strain N400 and of Aspergillus tubigensis strain NW756

The construction of a genomic library in the phage lambda replacement vector EMB4 from Promega Biotech Inc. of *Aspergillus niger* strain N400 (CBS 120.49) was in accordance with the procedure of Harmsen et al. (Harmsen, J. A. M.; Kusters-van Someren, M. A.; Visser, J.; Current Genetics 18:161–166 1990). The *Aspergillus tubigensis* NW756 genomic library as described by Bussink et al. (Bussink, H. J. D.; Buxton, F. P.; Visser, J.; Current Genetics 19:467–474 1991) was constructed by ligating partially Sau3A1-digested genomic DNA fragments into the phage lambda replacement vector EMBL3 cut with BamHI.

2. Screening of an Aspergillus niger genomic library for the FAE and the isolation thereof 2.1 Isolating a FAE fragment using PCR with synthetic oligonucleotide mixtures Details of molecular cloning techniques are described by Sambrook et al. in Molecular Cloning: A Laboratory Manual, 2nd edition (1989; Cold Spring Harbor Laboratory Press).

The amino acid sequence derived above was used to synthesize two degenerate oligonucleotide mixtures (shown as SEQ I.D. No. 4 and No. 5), one corresponding to the N-terminal amino acid sequence and one corresponding to an internal amino acid sequence. The oligonucleotides were synthesized by Isogen Bioscience, The Netherlands.

A PCR was performed using an equal amount of both oligonucleotide mixtures, Taq-polymerase (BRL) and 20 ng of chromosomal DNA of *Aspergillus niger* N400. The denaturing temperature was 95° C. for one minute, the annealing temperature was 50° C. for one minute and the extension temperature was 72° C. for one minute. 30 cycles were applied.

The reaction mixture was subjected to agarose gel electrophoresis. After separation a band of about 250 bp was observed. This fragment was isolated from gel using the GeneClean method (Bio101 Inc., USA).

2.2 Cloning and sequencing of the FAE fragment

The isolated DNA fragment was cloned in the pGEM-T Vector system (Promega Biotech Inc.). Sequence analysis of this fragment was performed using a T7-sequencing kit (Pharmacia). The results of the sequence analysis demonstrate a sequence in which both of the oligonucleotide sequences can be detected.

In SEQ. I.D. No. 6 the nucleotide at position 9 does not match with the nucleotide at position 9 for SEQ.I.D. No. 4 possibly because of an error in primer synthesis or in the sequencing. Also, in SEQ. I.D. No. 6 the amino acid at position 72 does not match with the amino acid at position 7 for SEQ.I.D. No. 2 possibly because of an error in the amplification or in the sequencing.

Translation of the complete nucleic acid sequence of this fragment into a putative amino acid sequence produces a sequence (shown as Sequence I.D. No. 7) in which all three amino acid sequences shown as SEQ I.D. No.s 1–3 can be detected (apart from the aforementioned errors).

2.3 Screening of an *Aspergillus niger* genomic library for the FAE gene

For the screening of the *A. niger* genomic library, $2\times10^3$ pfu per plate were plated on five plates of 15 cm diameter using *E. coli* LE 392 as plating bacterium. LM (10 g/l trypton, 5 g/l yeast extract, 10 mM NaCl, 10 mM $MgCl_2$) medium plus 1.5% agar or 0.6% agarose were used for the bottom and top layer, respectively.

After an overnight incubation of the plates at 37° C., duplicate filters (Hybond-N, Amersham) were prepared from each plate.

The DNA was cross-linked to the filters by UV-treatment for 2 minutes. The filters were then prehybridized for three hours and screened with the 256 bp FAE fragment using hybridization and washing conditions similar for those used for Southern blot hybridizations (hybridization temperature was 65° C., washing conditions were 2×20 minutes in 2×SSC (prepared from 20×SSC, which comprises 3M NaCl and 0.3M sodium citrate), 0.5% SDS followed by 2×20 minutes in 0.2×SSC (0.5% SDS).

Four positive phages were isolated from the plate using a Pasteur pipet and the phages were eluted from the agar plug in 500 ml SM buffer (which comprises per litre: 5.8 g NaCl, 2 g $MgSO_4 \cdot H_2O$, 50 ml of 1M Tris.HCl pH 7.5 and 5 ml of 2% (472) gelatin), containing 10 µl chloroform. The phages obtained were purified using the procedure described above with duplicate filters from plates each containing 50–100 plaques of the phages isolated.

After purification, the phages were propagated by plating out until confluent plates were obtained. The phages were eluted by adding 3 ml SM buffer and intermittent shaking for two hours. The buffer containing the phages was transferred to eppendorf tubes and centrifuged for 5 minutes at maximum speed in an eppendorf centrifuge to remove bacteria. The supernatant was transferred to a new eppendorf tube, 20 µl chloroform was added and the number of pfu was determined. These phage stocks contained approximately $5 \times 10^9$ pfu/ml.

2.4 Restriction analysis of FAE containing phages

From each of the isolated phages, DNA was isolated according to the method of Sambrook et al (ibid). The isolated DNA was analyzed by Southern analysis using the following restriction enzymes: BamHI; EcoRI; HinDIII; SalI; XbaI; PstI and XhoI. The DNA was digested for four hours at 37° C. After digestion the fragments were separated by agarose gel electrophoresis at 50 V for 6 hours.

After electrophoresis, the DNA was denatured and transferred to a nitro-cellulose membrane (Hybond-N, Amersham). Prehybridization, hybridization and washing were performed as described above.

In this way preliminary restriction maps were constructed and fragments hybridizing to the 256 bp FAE fragment were selected for cloning.

3. Subcloning of the FAE gene

Four DNA fragments from the isolated phages described above were selected for subcloning of the FAE gene:

a 3 kb EcoRI fragment present in phage 2, a 6 kb EcoRI fragment present in phage 1, 3 and 4, a 9 kb SalI fragment present in all four phages, and a 4 kb XhoI fragment present in phage 1.

A 0.5 kb SalI-PstI fragment is present in Phage 1 and a 1.5 kb PstI-HinDIII fragment is present in Phage 2.

Excision of the FAE sequences from Phage 1 and Phage 2, and the subsequent combination thereof results in the complete FAE gene (see above commentary). Each of Phages 3 and 4 comprises partial sequences of the FAE gene.

20 µg of phage DNA was digested for four hours with 50 units of the selected restriction enzymes at 37° C. The fragments were separated by agarose gel electrophoresis and isolated by the GeneClean method (Bio101 Inc.).

The fragments were ligated in vector pbluescript SK+ cut with the corresponding enzyme. Ligations were performed overnight at 16° C. with T4 DNA-ligase (BRL). The ligation mixes were transferred to E.coli DH5α and grown overnight on LB (10 g/l NaCl, 10 g/l Trypton, 5 g/l Yeast Extract, 1.5% agar) plates containing 50 µg/ml Ampicillin, 0.1% X-gal and 5 mM IPTG.

Per ligation, 5 white transformants were selected and grown overnight in 5 ml LB (10 g/l NaCl, 10 g/l Trypton, 5 g/l Yeast Extract) medium at 37° C.

Plasmid DNA was isolated from the cultures by the alkaline lysis method (Sambrook et al—ibid).

4. Sequencing

The sequence of the A. niger FAE gene was determined by sequencing the subcloned fragments. Sequencing was performed by the dideoxynucleotide chain termination procedure (Sanger et al. 1977 Prc. Natl. Acad. Sci. USA 74, 5463–5467) using a T7 DNA polymerase sequencing kit from Pharmacia. Subclones for DNA sequencing were constructed in M13 mp18/19 (Messing, 1983 Meth. Enzymol. 101C, 20–78) using universal or specific oligonucleotides as primers.

The sequences obtained were analysed with the University of Wisconsin software (Deveroux et al. 1984 A comprehensive set of sequence analysis programs for the Vax. Nucl. Acids. Res. 12, 387–395).

5. Transformation

A. niger can be transformed with the FAE gene using the transformation procedure of de Graff et al. (1992). Alternatively, the transformation of A. niger can be based on the teachings of Buxton, F. P., Gwynne D. I., Davis, R. W. 1985 (Transformation of Aspergillus niger using the argB gene of Aspergillus nidulans. Gene 37:207–214), Daboussi, M. J., Djeballi, A., Gerlinger, C., Blaiseau, P. L., Cassan, M., Lebrun, M. H., Parisot, D., Brygoo, Y. 1989 (Transformation of seven species of filamentous fungi using the nitrate reductase gene of Aspergillus nidulans. Curr. Genet. 15:453–456) and Punt, P. J., van den Hondel, C. A. M. J. J. 1992 (Transformation of filamentous fungi based on hygromycin B and Phleomycin resistance markers. Meth. Enzym. 216:447–457).

In this regard, for the purification of protoplasts, spores from one PDA (Potato Dextrose Agar—from Difco lab. Detroit) plate of fresh sporulated N400 (CBS 120.49, Centraalbureau voor Schimmelcultures, Baarn) (7 days old) are washed off in 5–10 ml water. A shake flask with 200 ml PDC (Potato Dextrose Broth, Difco 0549-17-9, Difco Lab. Detroit) is inoculated with this spore suspension and shaken (250 rpm) for 16–20 hours at 30° C.

The mycelium is harvested using Miracloth paper and 3–4 g wet mycelium are transferred to a sterile petri dish with 10 ml STC (1.2M sorbitol, 10 mM Tris HCl Ph 7,5, 50 Mm CaCl) with 75 mg lysing enzymes (Sigma L-2265) and 4500 units lyticase (Sigma L-8012).

The mycelium is incubated with the enzyme until the mycelium is degraded and the protoplasts are released. The degraded mycelium is then filtered through a sterile 60 µm mesh filter. The protoplasts are harvested by centrifugation 10 min at 2000 rpm in a swing out rotor. The supernatant is discarded and the pellet is dissolved in 8 ml 1.5M $MgSO_4$, and then centrifuged at 3000 rpm for 10 min.

The upper band, containing the protoplasts is transferred to another tube, using a transfer pipette and 2 ml 0.6M KCl is added. Carefully 5 ml 30% sucrose is added on the top and the tube is centrifuged 15 min at 3000 rpm.

The protoplasts, lying in the interface band, are transferred to a new tube and diluted with 1 vol. STC. The solution is centrifuged 10 min at 3000 rpm. The pellet is washed twice with STC, and finally solubilized in 1 ml STC. The protoplasts are counted and eventually concentrated before transformation.

For the transformation, 100 μl protoplast solution ($10^6$–$10^7$ protoplasts) are mixed with 10 μl DNA solution containing 5–10 μg DNA and incubated 25 min at room temperature. Then 60% PEG-4000 is carefully added in portions of 200 μl, 200 μl and 800 μl. The mixture is incubated 20 min at room temperature. 3 ml STC is added to the mixture and carefully mixed. The mixture is centrifuged 3000 rpm for 10 min.

The supernatant is removed and the protoplasts are solubilized in the remaining of the supernatant. 3–5 ml topagarose is added and the protoplasts are quickly spread on selective plates.

D. SCREENING OF OTHER ASPERGILLUS SPECIES FOR THE PRESENCE OF THE FAE GENE

Chromosomal DNA was isolated from A.niger N400 (CBS 120.49), A.nidulans WG096, A.tubigensis NW756, A.niger var. awamori 407.9 (CBS 115.52), A. aculeatus 489.16 (CBS 610.78), A.japonicus (CBS 114.51), A.oryzae 422.5 (ATCC 203.86), A.sojae 363.9 (ATCC 202.35), A.carbonarius 277.11 (CBS 420.64) and A.tubigensis 3M43 (Danisco collection). 3 μg of DNA was digested with BamHI, separated on agarose gel electrophoresis and transferred to a nitrocellulose membrane. Southern hybridization was performed on the filter with the 244 bp FAE fragment (SEQ. I.D. No. 6) at 56° C. The filter was washed 3×20 minutes with 4×SSC, 0.5% SDS. All species tested showed hybridizing bands with the 244 bp FAE fragment (SEQ. I.D. No. 6), indicating the presence of similar genes in all these fungal species.

E. ANTIBODY PRODUCTION

Antibodies against the purified FAE were prepared as described by v. d. Veen et al (Arch Microbiol 157 p23–28 (1991)). In this regard, antibodies against the pure enzymes were raised in Balb/c mice as follows: equal volumes of filter sterilised phosphate buffered saline (PBS) and Freund's complete adjuvant (Difco, Detroit, USA) were vortexed for 4 h at room temperature. Desalted, lyophilised purified protein (50μg) was dispersed in approx. 300 μl of adjuvant emulsion. This mixture was vortexed and immediately injected intraperitoneally into a mouse. Seven weeks after immunisation the mice were boosted by intraperitoneal injection of an emulsion of PBS and incomplete adjuvant (Difco) containing 25 μg of purified protein per mouse. After seven days, blood samples were taken and serum recovered. Six weeks after sampling, the mice were again boosted and seven days later they were bled. Antisera were stored at −70° C. Incubation of nitrocellulose blots with the specific antisera followed by staining with alkaline phosphatase labelled goat anti-mouse IgG was done as described by the manufacturer (Bio-Rad).

F. USES OF FAE WITH OXIDATIVE ENZYMES

In the following experiments the FAE enzyme of the present invention is used in a wheat dough supplemented with oxidative enzymes, in particular glucose oxidase ("GOX") which can be used to generate hydrogen peroxide in situ. In these experiments, which are described below, the FAB is added for the generation of free FA. Preliminary tests show that this combination system of enzymes is indeed feasible as it yields beneficial results with dough and the like.

The effect of adding GOX/POD (peroxidase) and FAE to weak wheat flour was investigated by measuring the strength and extensibility of a dough prepared from the flour. The amounts of enzymes and the results are shown in Table 2—shown below.

TABLE 2

Extensiograph measurement of the effect of FAE/GOX/POD on wheat dough

| Enzyme dosage | FU | Dough resistance | | | Extensibility | | |
|---|---|---|---|---|---|---|---|
| | | 45' | 90' | 135' | 45' | 90' | 135' |
| GOX 200 U POD 2700 U | 500 | 280 | 410 | 490 | 154 | 134 | 116 |
| GOX 200 U POD 2700 U FAE 39 U | 520 | 290 | 430 | 500 | 149 | 135 | 124 |
| GOX 200 U POD 2700 U FAE 3.9 U | 520 | 270 | 420 | 500 | 152 | 132 | 119 |

Enzyme units refer to units per. kg flour. FIGS. 45', 90' and 135' refer to time in minutes after preparation of the dough. FU are farinograph units and are indicative of the strength (firmness) of the dough. No additives were used. The water absorption of the flour was 52%. The trials were performed under conditions prescribed by AACC for extensiograph measurements (Extensiograph Method, General, AACC Method 54–10).

The data in Table 2 show that the combination of FAE with the oxidative system leads to an increase in the strength of the dough as indicated by an increase in farinograph units. This result was confirmed by an increase in dough resistance—i.e. the strength of the dough. The results further indicate that a high dosage of FAE leads to a better extensibility of the dough and a higher water absorption.

Without wishing to be bound by theory, it is believed that in this combination system the liberated FA may be a good substrate for POD readily forming radicals that may initiate formation of other radicals, e.g. amino acids in the protein fraction. Another explanation for the positive effect seen when FAE is added to an oxidative system might be that FA stabilises the POD which would be in accordance with Halliwell, B. (1978) (Planta 140, 81–88).

G. USES OF FAE IN HYDROLYSIS REACTIONS

In the following experiments the FAE enzyme of the present invention is used to hydrolyse wheat bran. In this regard, we have found that it is possible to improve the breakdown of the cell wall structure enzymatically by using a combination of FAE and xylanase. The experiments that show this effect are outlined in Table 3—shown below.

TABLE 3

Enzymatic hydrolysis of wheat bran

| Enzyme dosage (U/g bran) | Solubilised Wheat Bran (% w/w) |
|---|---|
| control | 28.06 |
| 1.2 U FAE | 27.73 |
| 104 U xylanase | 28.70 |
| 1.2 U FAE + 104 U xylanase | 33.20 |

Enzymes were added to a suspension of wheat bran (5%) in acetate buffer, 50 mM, pH 5. The sample was incubated at 35° C. for 4 hours and centrifuged. The supernatant was freeze dried, and the dry matter content was determined.

The results of the enzyme hydrolysis of wheat bran shown in Table 3 show that FAE acts synergistically with xylanase in the solubilisation of wheat bran in a suspension. This breakdown of the cell wall by enzyme addition might lead to improved baking properties of bran. Similar beneficial results on addition of the FAE of the present invention would be expected for bread and the like prepared from other cereals like rye and oat which also contain significant levels of FA.

H. USES OF FAE IN THE PREPARATION OF FOOD AND FEED

The FAE of the present invention may be used in the partial breakdown of cell wall material in feed. In this regard, it is known that xylanase is commonly used in wheat and rye based feed for chicken in order to diminish the viscosity of the intestine fluid—and thereby increase the utilisation of feed and avoid sticky droppings. Addition of the FAB of the present invention may open the xylan structure and thereby to increase the access of xylanase to the xylan polymers.

Ferulic and coumaric acids are believed to cross-link hemicelluloses and lignin in forage (Helm & Ralph, 1993, J. Agric. Food Chem. 41:570–576 1993). The addition of the FAE of the present invention to forage may increase the value of the forage by opening the cell wall structure and thereby enhancing the efficiency of breakdown in the gastrointestinal tract of animals.

I. USES OF FAE TO PREPARE VANILLIN

It is known that free FA can be converted to vanillin by vanilla plant root material, as described in WO 94/13614 or by microorganisms (Falconnier, B. et al. (1994) J. Biotechnol. 37, 123–132 and Hagedorn, S. and Kaphammer, B. (1994), Annu. Rev. Microbiol. 48, 773–800). Thus the FAE of the present invention can be used for the preparation of FA from FA containing material, such as sugar beet and corn cob meal. Once the FA has been extracted it can then be biotransformed into vanillin. In this regard, the high content of FA in sugar beet 0.8% (our measurement) and corn cob meal 1.1% (our measurement) makes these good sources of FA for vanillin production.

SUMMARY

The present invention therefore relates to the purification of a FAE from *A. niger*. In addition the present invention relates to the isolation and sequence determination of the gene coding for the FAE.

The enzyme of the present invention is useful as it can be used alone or in combination with one or more other POIs to improve processes for preparing or treating plant material, foodstuffs and feeds as well as the foodstuffs and feeds themselves. For example, the FAE can be used in and in the preparation of wheat based products. The FAE can also be used in other FA containing plant material.

Other modifications of the present invention will be apparent to those skilled in the art without departing from the scope of the present invention.

We claim:

1. An enzyme system comprising an isolated purified ferulic acid esterase (FAE) and at least one enzyme of interest (EOI), wherein the FAE comprises the amino acid sequences of SEQ ID NOs: 1 and 2.

2. An enzyme system comprising an isolated and purified ferulic acid esterase (FAE) and at least one enzyme of interest (EOI), wherein the FAE comprises the amino acid sequences of SEQ ID NOs: 1, 2 and 3.

3. The enzyme system as in any one of claims 1 or 2 wherein the EOI is an oxidative enzyme.

4. The enzyme system as in any one of claims 1 or 2 wherein the EOI is a polysaccharide modifying enzyme, a protease or an acetyl esterase.

5. The enzyme system as in any one of claims 1 or 2 wherein the EOI is a polysaccharide modifying enzyme selected from the group consisting of a xylanase, an arabinase, a glucanase, a pectinolytic enzyme and a rhamnogalacturonase.

6. The enzyme system as in any one of claims 1 or 2 wherein the FAE is a recombinant FAE.

7. An isolated and purified ferulic acid esterase (FAE) comprising the amino acid sequences of SEQ ID NOs: 1 and 2.

8. An isolated and purified ferulic acid esterase (FAE) comprising the amino acid sequences of SEQ ID NOs: 1, 2 and 3.

* * * * *

UNITED STATES PATENT AND TRADEMARK OFFICE
CERTIFICATE OF CORRECTION

PATENT NO.   : 6,143,543
DATED        : November 7, 2000
INVENTOR(S)  : Michelsen et al.

It is certified that error appears in the above-identified patent and that said Letters Patent is hereby corrected as shown below:

<u>Column 7,</u>
Lines 46-47, please change "glyceride oligomers" to -- glucoside oligomers --.

Signed and Sealed this

Thirteenth Day of May, 2003

JAMES E. ROGAN
*Director of the United States Patent and Trademark Office*